(12) United States Patent
Mizunuma et al.

(10) Patent No.: US 8,021,152 B2
(45) Date of Patent: Sep. 20, 2011

(54) DENTAL HANDPIECE

(75) Inventors: Masanori Mizunuma, Kanuma (JP); Takao Kimura, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 337 days.

(21) Appl. No.: 12/144,801

(22) Filed: Jun. 24, 2008

(65) Prior Publication Data
US 2008/0318185 A1 Dec. 25, 2008

(30) Foreign Application Priority Data

Jun. 25, 2007 (JP) .................................. 2007-166113
May 27, 2008 (JP) .................................. 2008-137917

(51) Int. Cl.
*A61C 1/08* (2006.01)
(52) U.S. Cl. ........................................ 433/126; 433/127
(58) Field of Classification Search .................... 433/82, 433/114, 115, 116, 117, 118, 124, 126, 127, 433/128, 129, 133
See application file for complete search history.

(56) References Cited

U.S. PATENT DOCUMENTS

| 4,278,428 A | 7/1981 | Straihammer et al. |
| 4,382,790 A | 5/1983 | Loge et al. |
| 6,398,551 B1 | 6/2002 | Schatz et al. |
| 2004/0014000 A1 | 1/2004 | Bernhard |

FOREIGN PATENT DOCUMENTS

| JP | 7-51136 | 6/1995 |
| JP | 2005-342403 A | 12/2005 |

*Primary Examiner* — Cris L Rodriguez
*Assistant Examiner* — Eric Rosen
(74) *Attorney, Agent, or Firm* — Jason D. Voight (57) ABSTRACT

A dental handpiece having a grip with a head in which a treatment tool may be detachably attached. A front casing portion of the grip is continuous to a rear casing portion at an obtuse angle. A first rotary shaft is rotatably supported in the rear casing portion. A cylindrical jacket extends from the head and is arranged in the front casing portion toward the first rotary shaft. A second rotary shaft is rotatably supported in the jacket, and is operatively connected to the treatment tool at one end and to the first rotary shaft at the other end via a gear. The rotary shafts transmit driving force to the head section to drive the treatment tool. The jacket is provided with an engagement groove on its circumferential surface. An engaging device disposed in the rear casing portion detachably engages the groove, thereby fixing the jacket in the front casing portion.

14 Claims, 7 Drawing Sheets

DENTAL HANDPIECE

FIELD OF ART

The present invention relates to a dental handpiece, more specifically, a contra-angle dental handpiece.

BACKGROUND ART

Figure 9:
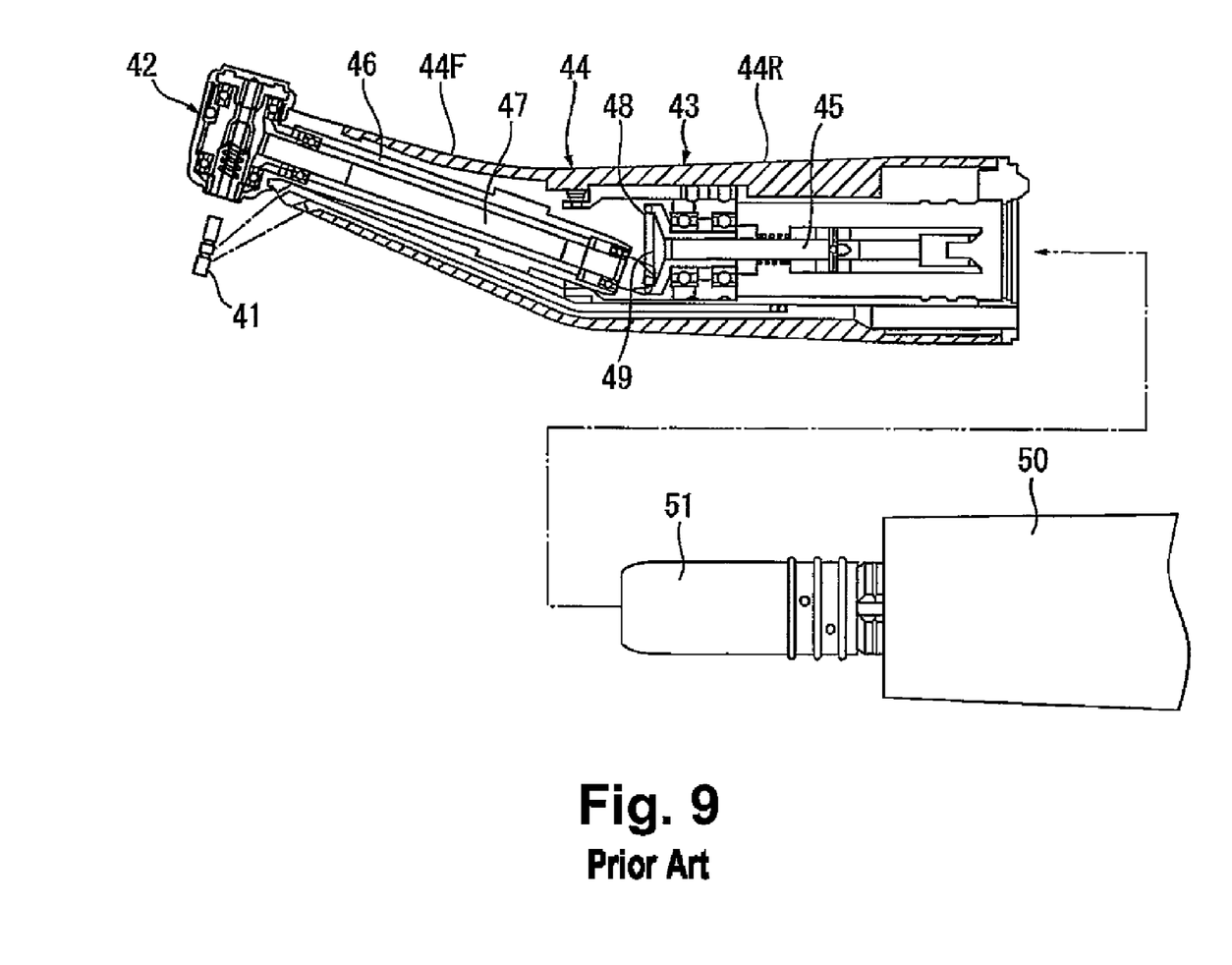
FIG. 9 is a longitudinal sectional view of a conventional dental handpiece.

Conventional dental handpieces are known, for example, from JP-2005-342403-A. FIG. 9 shows a dental handpiece disclosed in this publication, which includes a grip section 43 having a head section 42, to which a treatment tool 41 is detachably attached, and a motor casing (drive section) 50 detachably connected to the grip section 43. This dental handpiece is of a contra-angle type, wherein the casing of the grip section 44 includes a front casing portion 44F continuous to a rear casing portion 44R obliquely at an obtuse angle. In the rear casing portion 44R, a first rotary shaft 45 is rotatably supported, and in the front casing portion 44F, a cylindrical jacket 46 extending from the head section 42 is inserted toward the first rotary shaft 45 and fixed. The jacket 46 rotatably supports therein a second rotary shaft 47, which is operatively connected to the treatment tool 41 and linked to the first rotary shaft 45 via gears 48 and 49. A motor shaft 51 extends from the motor casing 50, and drivingly connected to the first rotary shaft 45. In this manner, the driving force of the motor in the motor casing 50 is transmitted by means of the first and second rotary shafts 45 and 47 to the head section 42, where the treatment tool 41 is driven.

In this type of dental handpiece, the jacket inserted into the front casing portion is fixed therein conventionally by means of a screw which is fastened into a screw hole provided through the peripheral surface of the front casing portion, as shown, for example, in FIG. 4 of JP-7-51136-B. However, as the handpiece is used, the screw is loosened, which causes the head section to shake. This impairs the operability of the handpiece and makes the treatment hard for the practitioner.

In addition, this type of dental handpiece enjoys excellent appearance due to the good design of its casing. However, the screw exposed on the peripheral surface of the casing impairs the appearance of the handpiece.

SUMMARY OF THE INVENTION

The present invention aims to solve such problems in the prior art. It is therefore an object of the present invention to provide a dental handpiece in which the jacket inserted into the grip casing is fixed therein by a reliable means in place of a conventional screw, to thereby improve the durability and appearance of the dental handpiece.

According to the present invention, there is provided a dental handpiece comprising:

a grip section having a head section in which a treatment tool is detachably attached, and a drive section detachably connected to the grip section, said grip section further comprising:

a casing having a front casing portion and a rear casing portion, with said front casing portion being continuous to said rear casing portion at an angle, a first rotary shaft rotatably supported in the rear casing portion, a cylindrical jacket extending from the head section, and arranged and fixed in the front casing portion toward said first rotary shaft, and a second rotary shaft rotatably supported in said jacket, and operatively connected to the treatment tool at one end and to said first rotary shaft at the other end via a gear, wherein driving force from said drive section is transmitted by means of said first and second rotary shafts to the head section to drive the treatment tool, characterized in that said jacket is provided with an engagement groove on its circumferential surface, said grip section further comprises engaging means disposed in the rear casing portion and detachably engaging said engagement groove on the jacket, wherein said jacket arranged in the front casing portion is fixed therein by means of engagement of said engagement groove on the jacket and said engaging means in the rear casing portion.

The grip section may further include a cylindrical outer jacket fixed on the circumferential surface of the jacket. The engagement groove on the jacket may preferably include a circumferential groove provided in the circumferential surface of the jacket at a location facing to the interior of the rear casing portion, and a slot formed through the outer jacket at a location corresponding to and allowing access to the circumferential groove of the jacket. On the other hand, the engaging means may preferably include an engagement rod arranged in the rear casing portion generally in parallel with the first rotary shaft and displaceable toward the front casing portion, and engagement fixing means for fixing the engagement rod.

The circumferential groove of the jacket and the tip of the engagement rod may be formed so as to interfit with each together, and the slot in the outer jacket maybe formed such that the circumferential surface of the engagement rod is capable of contacting the upper edge of the slot.

The engagement fixing means for fixing the engagement rod may preferably include a threaded portion formed in a circumferential surface of the engagement rod, and a nut fixed in the rear casing portion and receiving the engagement rod therethrough, with the threaded portion of the engagement rod screwed together in the nut.

The engagement rod may preferably have on its rear end face a tool engaging portion in which a driving tool is engageable.

In another embodiment, the grip section may include an annular or cylindrical member fit on and attached around the jacket at a location facing to the interior of the rear casing portion, and the engagement groove on the jacket may include a slit formed in the circumferential surface of the annular or cylindrical member. The engaging means may include an engagement rod arranged in the rear casing portion generally in parallel with the first rotary shaft and displaceable toward the front casing portion, and engagement fixing means for fixing the engagement rod.

The annular or cylindrical member may preferably have a plurality of dents in its inner surface for holding a plurality of elastic balls therein. The annular or cylindrical member may be attached around the jacket via the balls, with the dents being capable of pressing the balls toward the central axis of the jacket.

The grip section may further include a sleeve provided on the inner surface of the rear casing portion, and a spring member arranged between the sleeve and the annular or cylindrical member for thrusting the annular or cylindrical member toward the head section.

The engagement fixing means for fixing the engagement rod may preferably include a threaded portion formed in the circumferential surface of the engagement rod, and a nut provided on the circumferential surface of the sleeve and receiving and guiding the engagement rod therethrough, with the threaded portion of the engagement rod screwed together in the nut.

In the dental handpiece according to the present invention, the jacket arranged in the front casing portion may be fixed therein by reliable means in place of a screw, so that the durability and appearance of the handpiece may be improved.

PREFERRED EMBODIMENTS OF THE INVENTION

The present invention will now be explained in detail with reference to the attached drawings.

Figure 1:
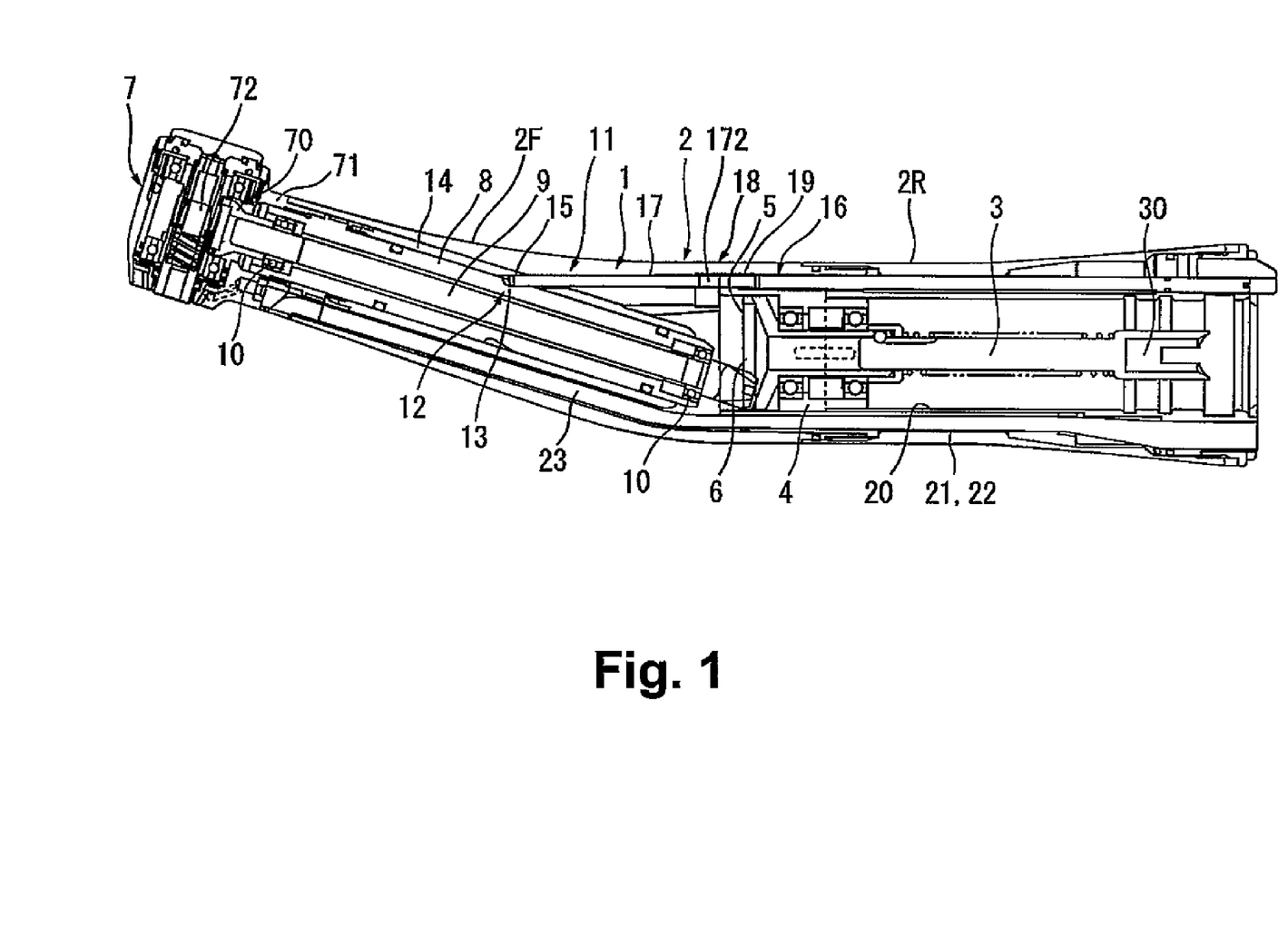
FIG. 1 is a longitudinal sectional view of head and grip sections of a dental handpiece according to an embodiment of the present invention.

FIG. 1 shows head and grip sections of a dental handpiece. As illustrated, the head section 7 has a bur sleeve 72, in which a treatment tool (see FIG. 4) is detachably fit. In the outer surface of the head section 7, an opening 70 is formed, and from around the opening, a sleeve 71 projects. A cylindrical jacket 8 is fixedly connected to the sleeve 71, and rotatably supports therein a second rotary shaft 9 via bearings 10. The second rotary shaft 9 is operatively linked to the bur sleeve 72 in the head section 7.

The grip section 1 has a cylindrical casing 2, which includes a front casing portion 2F and a rear casing portion 2R. The front casing portion 2F is slanted at an obtuse angle with respect to the rear casing portion 2R, and continuous thereto.

In the rear casing portion 2R, first rotary shaft 3 is rotatably supported via bearing 4. The first rotary shaft 3 is provided at its rear end with a connecting part 30, which detachably engages a motor shaft of a motor casing (drive section), and at its front end with gears 5 and 6, which mesh with the second rotary shaft 9.

The jacket 8 running from the outer surface of the head section 7 is inserted into the front casing portion 2F toward the first rotary shaft 3, and the second rotary shaft 9 extending through the jacket 8 is connected to the first rotary shaft 3 via the gears 5 and 6. Here, the second rotary shaft 9 meshes with the gear 6 arranged in contact with the inner surface of the gear 5 of the first rotary shaft 3, and the second rotary shaft 9 rotates at a number of revolutions higher than that of the first rotary shaft 3.

In this way, the driving force of the motor is transferred via the first and second rotary shafts 3 and 9 to the head section 7 to drive the treatment tool.

Incidentally, in this embodiment, a chip air pipe 21, a water pipe 22, and optical fibers 23 are arranged in an outer channel 20 axially extending within the wall thickness of the casing 2 of the grip section 1.

In this embodiment, the jacket 8 inserted in the front casing portion 2F is fixed therein by means of engagement mechanism 11 in place of a conventional screw. The engagement mechanism 11 includes engagement groove 12 provided on the circumferential surface of the jacket 8, and engaging means 16 disposed in the rear casing portion 2R and detachably engageable in the engagement groove 12 on the jacket 8. The jacket 8 is fixed in the casing 2 through the engagement between the engagement groove 12 and the engaging means 16.

Figure 2:
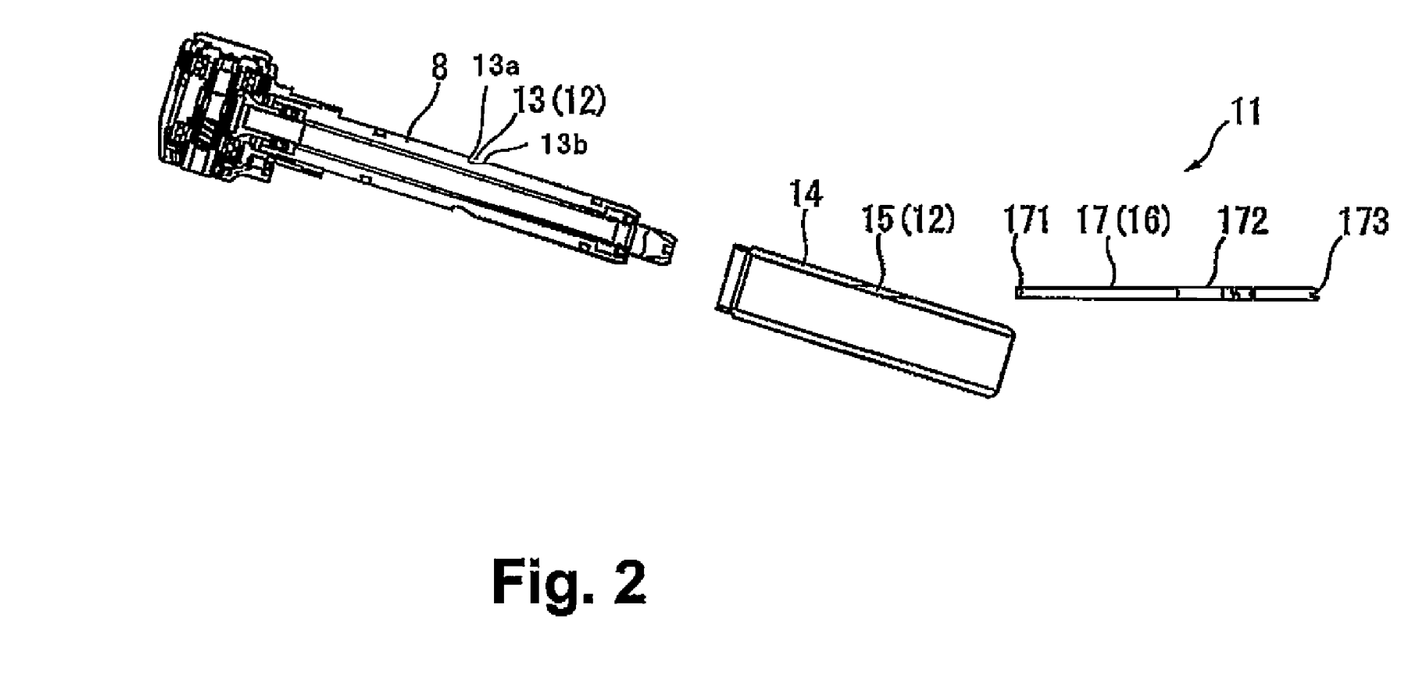
FIG. 2 is an exploded, longitudinal sectional view illustrating the engagement mechanism for fixing the jacket in the front casing portion, employed in the handpiece of FIG. 1.

FIG. 2 shows the structure of the engagement mechanism 11. In the illustrated embodiment of the engagement mechanism 11, the engagement groove 12 on the jacket 8 is composed of a circumferential groove 13 formed in the outer surface of the jacket 8, and a slot 15 formed in an outer jacket 14 at a location corresponding to the groove 13 of the jacket 8. The outer jacket 14 is in a cylindrical form, and disposed over and fixed on the outer surface of the jacket 8.

The groove 13 is formed in the circumferential surface of the jacket 8 at a location facing to the interior of the rear casing portion 2R at an angle with respect to the circumferential surface of the jacket 8 in the axial direction of the rotary shaft in the rear casing portion 2R. The groove 13 has an inclined surface 13a, to which the front end face of an engagement rod 17 of engaging means 16 to be discussed later abuts, and a slope surface 13b, with which the lower side of the outer surface of the tip portion of the engagement rod 17 may contact. The groove 13 is formed such that the tip portion of the engagement rod 17 is capable of fitting therein.

The slot 15 in the outer jacket 14 is a cylindrical bore in registry with the groove 13, and formed at an angle with respect to the outer surface of the outer jacket 14 in the axial direction of the rotary shaft in the rear casing portion 2R, and at a location corresponding to and allowing access to the groove 13 of the jacket 8. The slot 15 is formed such that generally the upper half of the edge of the slot 15 is capable of contacting the outer surface of the tip portion (the surface facing up) of the engagement rod 17 so that the engagement rod 17 at its outer surface of the tip portion slightly pushes the slot 15 upwards, while the slot 15 opens beyond the slope surface 13b of the groove 13 in the jacket 8, so that generally the lower half of the edge of the slot 15 is out of contact with the outer surface of the tip portion (the surface facing down) of the engagement rod 17.

The engaging means 16 includes the engagement rod 17 arranged in the rear casing portion 2R, and engagement fixing means 18 for fixing the engagement rod 17 in the rear casing portion 2R as shown in FIG. 1.

The engagement rod 17 is in the form of an elongate columnar rod, and has a tip portion slightly tapered (171) as shown in FIG. 2 so as to be fittable in the groove 13 on the jacket 8, a middle portion threaded at a predetermined location to form a threaded portion 172, and the rear end face provided with a tool engaging portion 173 in which a driving tool is engageable, in this case a slot for a driver.

The engagement fixing means 18 includes the threaded portion 172 formed in the axial middle portion of the circumferential surface of the engagement rod 17, and a nut 19 fixed in the rear casing portion 2R and receiving the engagement rod 17 therein to be screwed onto the threaded portion 172. The nut 19 is arranged in the rear casing portion 2R radially outside of a bearing 4, which is in proximity with the gears 5 and 6 on the front end of the first rotary shaft 3, with the nut axis lying in the direction of the first rotary shaft 3.

In this manner, the engagement rod 17 is arranged through the nut 19 in the rear casing portion 2R, and is axially displaceable toward the front casing portion 2F generally in parallel with the first rotary shaft 3. The tip of the engagement rod 17 engages in the groove 13 of the jacket 8 through the slot 15 in the outer jacket 14 in the front casing portion 2F, and this engagement is fixed by restricting the axial displacement of the engagement rod 17 through screwing together of the nut 19 and the threaded portion 172 of the engagement rod 17.

Figure 3:
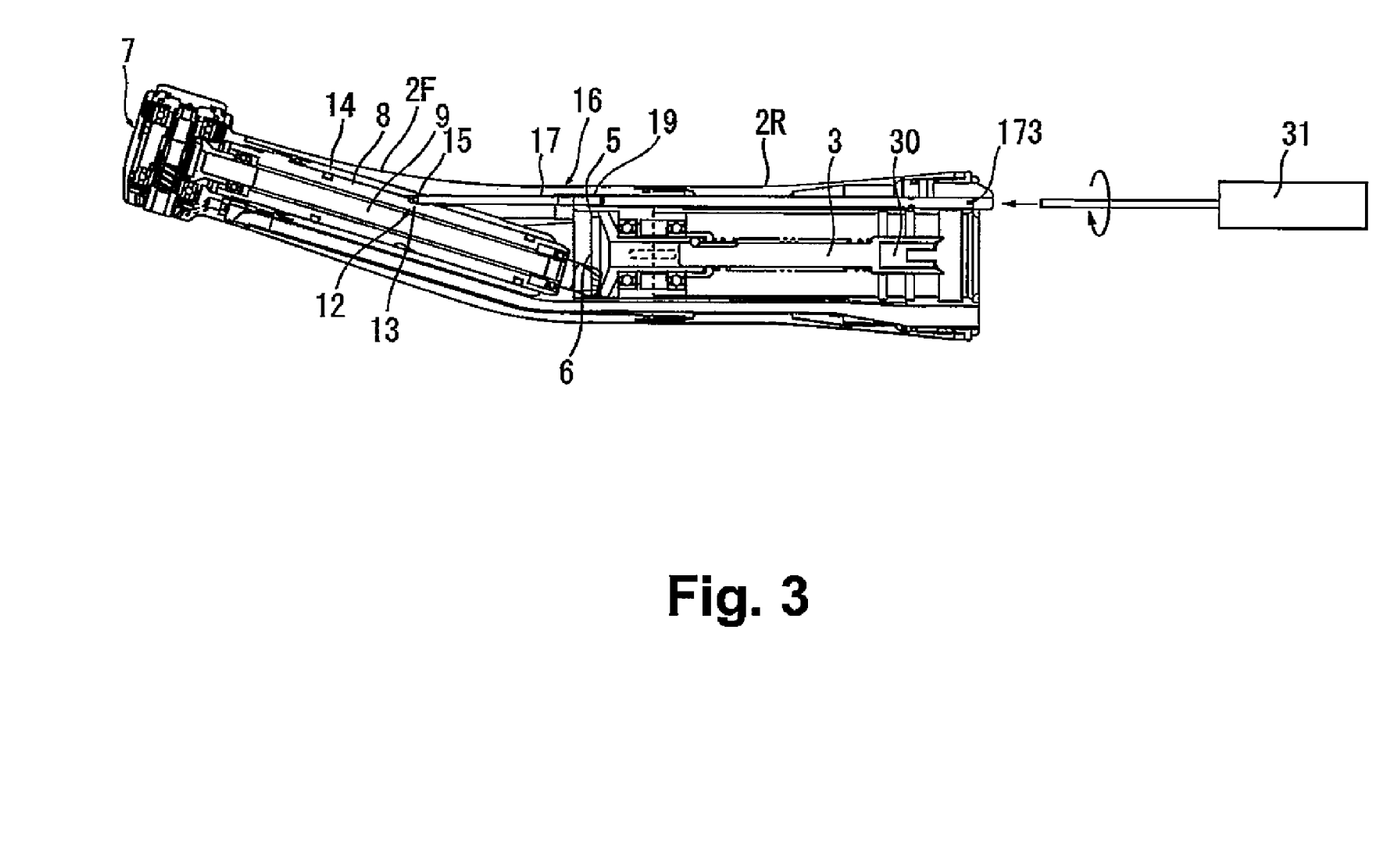
FIG. 3 is a longitudinal sectional view illustrating how the jacket inserted in the front casing portion is fixed therein by means of the engagement mechanism in the handpiece of FIG. 1.

In assembling, as shown in FIG. 3, the jacket 8 extending from the head section 7 is inserted into the front casing portion 2F, and the second rotary shaft 9 arranged in the jacket 8 is linked to the first rotary shaft 3 supported in the rear casing portion 2R via the gears 5 and 6. Then the engagement rod 17, which is arranged through the nut 19 in the rear casing portion 2R generally in parallel with the first rotary shaft 3, is screwed with a tool, such as a screw driver 31, fitted in the slot 173 in its rear end face. This makes the tip of the engagement rod 17 pass through the slot 15 in the outer jacket 14, and engage in the groove 13 of the jacket 8, with the outer jacket 14 being pressed slightly upwards with the surface of the engagement rod 17. The tip of the engagement rod 17 acts as a wedge in the groove 13 of the jacket 8. The engagement rod 17 presses the jacket 8 downwards as illustrated in FIG. 3 like a prop to prevent the jacket 8 from dropping out of the front casing portion 2F. At the same time, the downward pressure imposed on the jacket 8 by the engagement rod 17 is adjusted not to be excessive by the tip portion of the engagement rod 17 slightly pressing up the outer jacket 14, so that the jacket 8 is held at a predetermined position in the rear casing portion 2R, i.e., the position where the jacket 8 does not interfere with other parts in the front casing portion 2F.

As discussed above, the engagement groove 12 is provided on the circumferential surface of the jacket 8, and the engaging means 16 detachably engaging with the engagement groove 12 is provided in the rear casing portion 2R, and the jacket 8 arranged in the front casing portion 2F is fixed therein by means of the engagement between the engagement groove 12 on the jacket 8 and the engaging means 16 in the rear casing portion 2R. Thus the jacket 8 may be fixed in place with reliable means instead of a conventional screw, which improves the durability and appearance of the dental handpiece.

Further, the engagement groove 12 is composed of the groove 13, which is formed circumferentially in the outer surface of the jacket 8 at a location facing to the interior of the rear casing portion 2R, and the slot 15, which is formed in the outer jacket 14 fixed over the jacket 8 at a location corresponding to the groove 13. On the other hand, the engaging means 16 are composed of the engagement rod 17, which is arranged in the rear casing portion 2R generally in parallel with the first rotary shaft 3 and is axially displaceable toward the front casing portion 2F, and the engagement fixing means 18 for fixing the engagement rod 17. With such structures, reliable means for fixing the jacket 8 instead of a conventional screw may be realized in a simple manner.

Further, the groove 13 on the jacket 8 and the tip of the engagement rod 17 are made to be interfitting, and the slot 15 in the outer jacket 14 is formed such that the upper edge of the slot 15 is contacted with the circumferential surface of the engagement rod 17. With such structures, the jacket 8 may be pressed with the engagement rod 17 and prevented from dropping out of the front casing portion 2F, with the engagement rod 17 being arranged through the slot 15 in the outer jacket 14 and engaged at its tip in the groove 13 on the jacket 8. The jacket 8 may also be securely held in a predetermined position in the rear casing portion 2R, with the circumferential surface of the engagement rod 17 slightly pressing up the outer jacket 14.

The engagement fixing means 18 for the engagement rod 17 is composed of the threaded portion 172 formed on the circumferential surface of the engagement rod 17 and the nut 19 fixed in the rear casing portion 2R. With such a structure, the engagement fixing means 18 for the engagement rod 17 may be realized with a simple structure.

The rear end face of the engagement rod 17 is provided with the tool engaging portion (slot) 173, in which a driving tool, such as the driver 31 in this embodiment, is engageable. With such a structure, the engagement and disengagement of the engagement rod 17 in and out of the engagement groove 12 on the jacket 8 may be carried out easily with the driver 31 or the like tool, so that the head section 7 may easily be attached and detached to and from the casing 2 of the grip section 1.

Though in this embodiment, the engagement groove 12 on the jacket 8 is composed of the groove 13 in the circumferential surface of the jacket 8 and the slot 15 in the outer jacket 14, it is envisaged that the engagement groove 12 may alternatively be composed solely of a groove in the circumferential surface of the jacket 8, without the outer jacket 14 fixed on the jacket 8. In this case, it is preferred that the groove is given the function similar to the slot 15 in the outer jacket 14 either by its shape or by adding other means. Further, though the engaging means 16 is composed of the engagement rod 17 and the engagement fixing means 18, it is also envisaged that these may suitably be replaced with other equivalent functional components.

Figure 4:
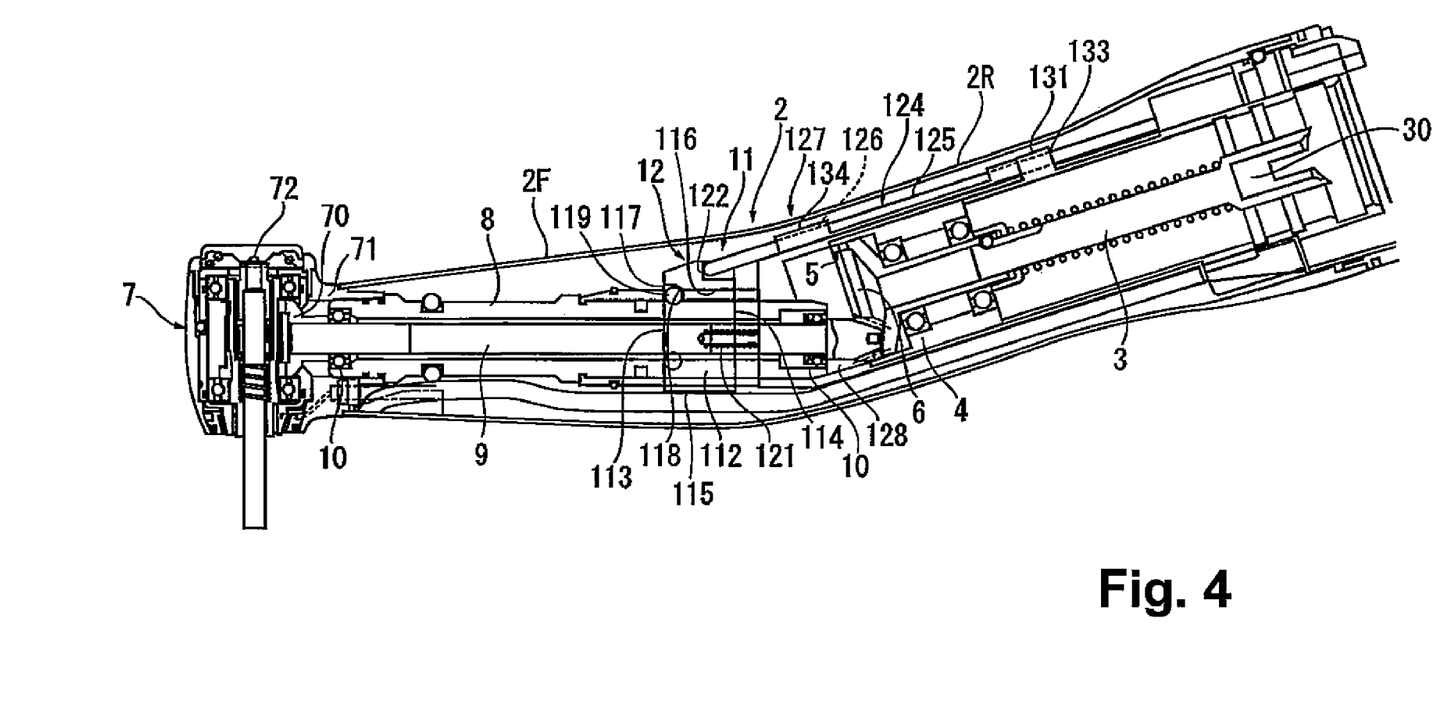
FIG. 4 is a longitudinal sectional view of head and grip sections of a dental handpiece according to another embodiment of the present invention.
Figure 5:
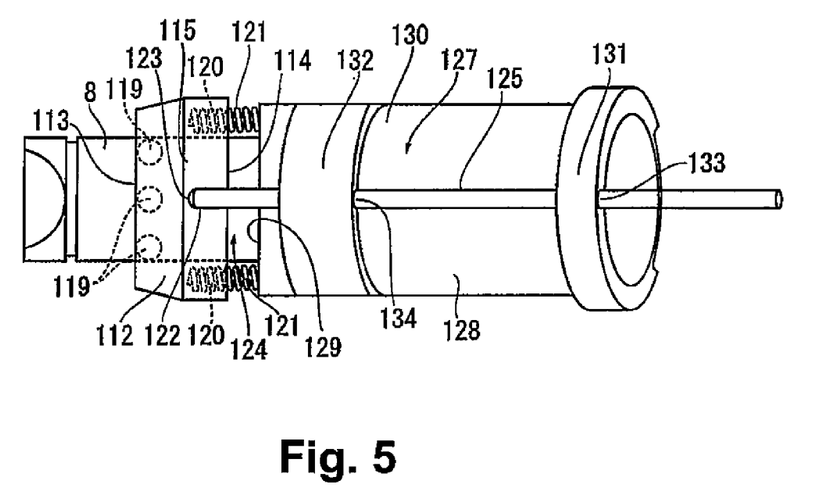
FIG. 5 is a plan view illustrating the engagement mechanism for fixing the jacket in the front casing portion, employed in the handpiece of FIG. 4.
Figure 6:
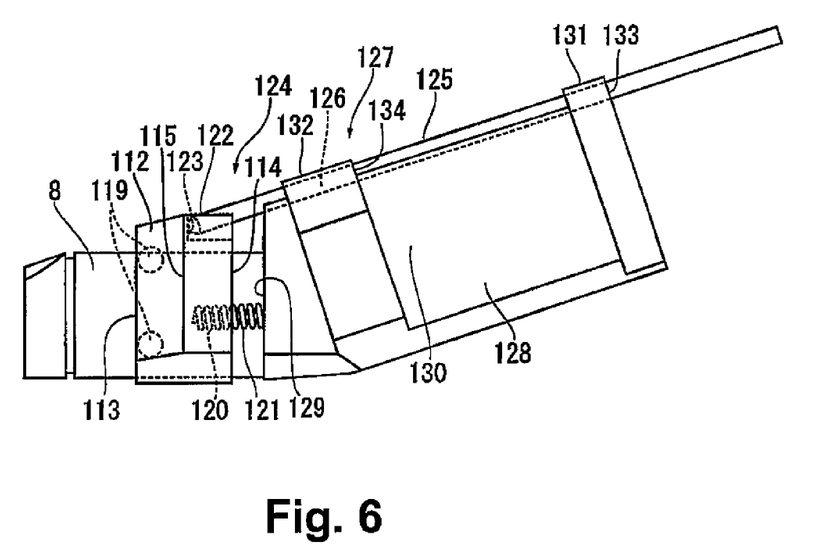
FIG. 6 is a side view of the engagement mechanism of FIG. 5.

FIG. 4 shows another embodiment of the engagement mechanism 11. In the illustrated embodiment of the engagement mechanism 11, the engagement groove on the jacket 8 is composed of a slit 122 formed on a base ring 112, which is fitted and fixed around the jacket 8. As shown in FIGS. 5 and 6, the base ring 112 is of an annular shape, and fittable on the circumferential surface of the jacket 8 at a predetermined location facing to the interior of the rear casing portion 2R. The base ring 112 has an inner diameter slightly larger than the outer diameter of the jacket 8 at the predetermined location. The base ring 112 also has an outer diameter at its front end slightly smaller than the outer diameter at its rear end, and the front half of the circumferential surface 115 of the base ring 112 on the side of the front end face 113 is tapered.

Figure 7:
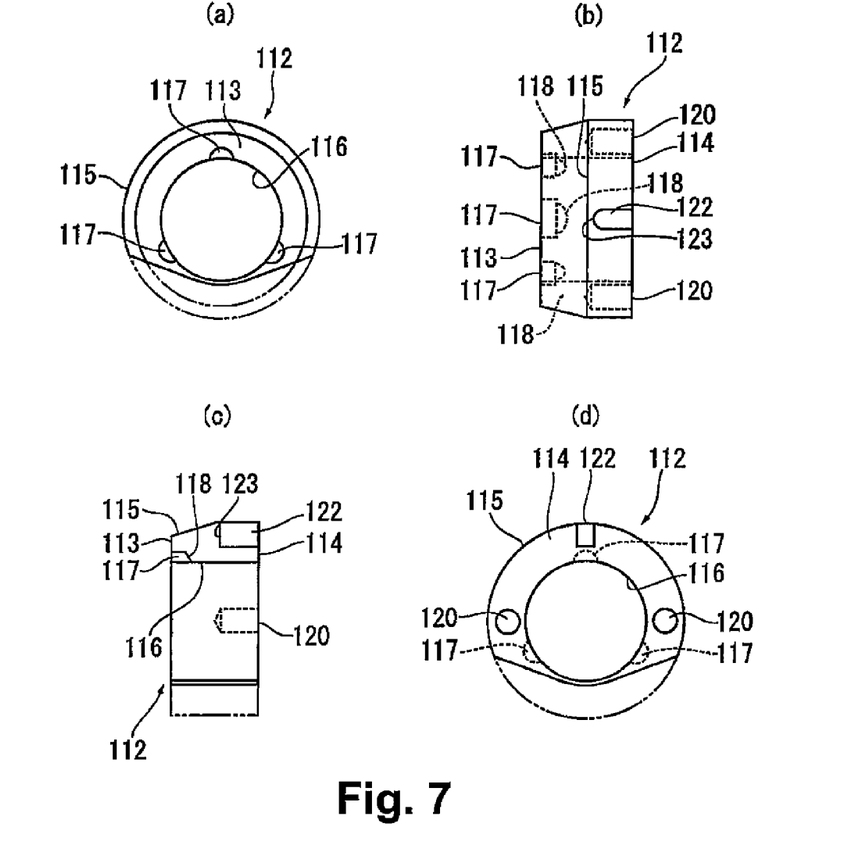
FIG. 7(a) is a front end view of the engagement mechanism, in particular the base ring.
FIG. 7(b) is a plan view thereof.
FIG. 7(c) is a longitudinal sectional view thereof.
FIG. 7(d) is a rear end view thereof.
Figure 8:
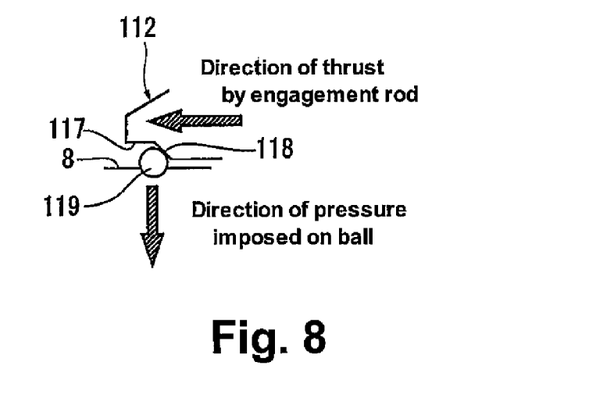
FIG. 8 is an explanatory view illustrating the effect of the base ring.

As shown in FIG. 7, in the inner surface 116 of the base ring 112 at its front end, a plurality of dents 117 are formed for accommodating and holding therein a plurality of balls 119 made of an elastic material, such as rubber. The dents 117 are arranged circumferentially at regular intervals. In the illustrated embodiment, three dents 117 for the ball are cut out axially from the front end face 113, and arranged in the front end face one at the top center and one on either side thereof at a 60° angular interval. As shown in FIG. 8, the innermost face 118 of the dent 117 is slanted so as to push the ball 119 in the dent 117 toward the radial center of the jacket 8, when the base ring 112 fit on the jacket 8 at a predetermined location is thrusted toward the head section 7.

As shown in FIG. 7, in the rear end face 114 of the base ring 112, two pits 120 each for receiving a coil spring 121 therein are arranged on the right and left side at 180° angular intervals.

The slit 122 is formed in the outer circumferential surface 115 of the base ring 112. The slit 122 is arranged in the rear end face 114 at the top center, and cut out in the outer circumferential surface 115 axially from the rear end face 114 so that the tip of an engagement rod 125 of engaging means 124 to be discussed later may be fit in the slit 122. The innermost face 123 in the slit 122 is formed at an angle, such as 90°, with respect to the axial direction of the base ring 112, such that the base ring 112 may be pushed toward the head section 7 with the engagement rod 125 abutting on the innermost face 123.

In this way, as shown in FIGS. 5 and 6, the base ring 112 is fitted and fixed around the jacket 8 arranged in the front casing portion 2F at a predetermined location facing to the interior of the rear casing portion 2R by means of the plurality of elastic balls 119 accommodated and held in the three dents 117. In each of the pits 120 in the rear end face 114 of the base ring 112, a coil spring 121 is inserted and projects rearward beyond the rear end face 114.

On the other hand, as shown in FIG. 4, the engaging means 124 includes an engagement rod 125 arranged in the rear casing portion 2R and engagement fixing means 127 for fixing the engagement rod 125 in the rear casing portion 2R. As shown in FIGS. 5 and 6, the engagement rod 125 is in the form of an elongate columnar rod, and has a tip portion so formed as to be fittable in the slit 122 on the base ring 112, a middle portion threaded at a predetermined location to form a threaded portion 126, and the rear end face provided with a tool engaging portion in which a driving tool is engageable, in this case a slot for a driver (not shown).

The engagement fixing means 127 includes the threaded portion 126 formed in the axial middle portion of the circumferential surface of the engagement rod 125, and nut 134 provided on the circumferential surface of a sleeve 128 disposed on the inner surface of the rear casing portion 2R and receiving the engagement rod 125 therein to be screwed onto the threaded portion 126 of the engagement rod 125.

The sleeve 128 is in the form of a cylinder fittable in the rear casing portion 2R, and has a front end face 129 slanted with respect to its longitudinal axis so as to face to the rear end face 114 of the base ring 112 in the front casing portion 2F. On the circumferential surface 130 of the sleeve 128, projecting steps 131 and 132 are formed at least in the top portion in the rear end portion and the axial middle portion, respectively. The step 131 in the rear end portion has a guide bore 133 formed therethrough for receiving therein and guiding the engagement rod 125 toward the slit 122 on the base ring 112. The step 132 in the axial middle portion has the nut 134 formed therethrough for receiving therein and guiding the engagement rod 125 in the same direction as the step 131, and screwed onto the threaded portion 126 on the engagement rod 125.

As shown in FIG. 4, the sleeve 128 is inserted and placed in the rear casing portion 2R in proximity with the base ring 112 in the front casing portion 2F, and rotatably supports the first rotary shaft 3 by means of a bearing 4 disposed therein. Between the sleeve 128 and the base ring 112, the coil springs 121 projecting beyond the rear end face 114 of the base ring 112 and contacting the front end face 129 of the sleeve 128 are compressed to uniformly thrust the base ring 112 toward the head section 7.

In this way, the engagement rod 125 is arranged in the rear casing portion 2R through the guide bore 133 and the nut 134 on the circumferential surface of the sleeve 128, generally in parallel with the first rotary shaft 3 and axially displaceably toward the front casing portion 2F. The tip of the engagement rod 125 engages in the slit 122 on the base ring 112 in the front casing portion 2F, which engagement is fixed by screwing together the threaded portion 126 of the engagement rod 125 and the nut 134 to restrict the axial displacement of the engagement rod 125.

In assembling, as shown in FIG. 4, the jacket 8 extending from the head section 7 is inserted into the front casing portion 2F, and the second rotary shaft 9 arranged in the jacket 8 is linked to the first rotary shaft 3 supported in the rear casing portion 2R via the gears 5 and 6. Then the engagement rod 125, which is arranged through the guide bore 133 and the nut 134 provided on the circumferential surface 130 of the sleeve 128 in the rear casing portion 2R, is screwed with a tool, such as a screw driver, fitted in the slot in its rear end face. This makes the tip of the engagement rod 125 engage in the slit 122 on the base ring 112 and press the base ring 112 in the direction of the second rotary shaft toward the head section 7. The pressure imposed by the engagement rod 125 also makes the innermost faces 118 of the dents 117 in the inner surface 116 of the base ring 112 press the balls 119 held therein toward the radial center of the jacket 8. In this way, the engagement rod 125 positions and presses downward the jacket 8 like a prop to prevent the jacket 8 from dropping out of the front casing portion 2F. At the same time, the base ring 112 is pressed onto the jacket 8 via the balls 119, so that the jacket 8 is reliably inhibited from shaking vertically and laterally with respect to the longitudinal axis. This state is more securely maintained by uniformly pressing the base ring 112 toward the head section 7 by means of the coil springs 121 compressed between the sleeve 128 and the base ring 112.

In this alternative way, the jacket 8 may also be fixed in place with reliable means instead of a conventional screw, which improves the durability and appearance of the dental handpiece, as with the previous embodiment.

In this embodiment, the engagement groove for the jacket 8 is provided in the form of the slit 122 formed in the circumferential surface of the base ring 112 which is fitted and fixed around the jacket 8 at a predetermined location facing to the interior of the rear casing portion 2R. The engaging means 124 includes the engagement rod 125, which is threaded on the circumferential surface to form the threaded portion 126. The guide bore 133 and the nut 134 for the engagement rod 125 are formed on the circumferential surface of the sleeve 128 disposed on the inner surface of the rear casing portion 2R. The engagement rod 125 is passed through the guide bore 133 on the sleeve 128 and the threaded portion 126 of the engagement rod 125 is screwed into the nut 134, so that the engagement rod 125 is arranged displaceably toward the front casing portion 2F generally in parallel with the first rotary shaft 3 to engage the tip of the engagement rod 125 in the slit 122 in the base ring 112. With such structures, reliable means for fixing the jacket 8 in place of a conventional screw may be realized in a simple manner.

Further, the base ring 112 is fitted and fixed around the jacket 8 via the plurality of balls 119, and pressed by the engagement rod 125 toward the head section 7 in the axial direction of the second rotary shaft 9, which also presses the balls 119 in the inner surface of the base ring 112 toward the radial center of the jacket 8. With such structures, the engagement rod 125 acting as a proppositions and securely presses the jacket 8 to prevent it from dropping out of the casing 2, and the jacket 8 is reliably inhibited from shaking. Moreover, since the base ring 112 is uniformly pressed toward the head section 7 by means of the coil springs 121 interposed between the sleeve 128 and the base ring 112, the effects of preventing the jacket 8 from dropping and shaking may be improved even more.

In this embodiment, the engagement groove for the jacket 8 is formed as the slit 122 in the circumferential surface of the annular base ring 112. However, this annular member may be replaced with a cylindrical member which is given generally the same structure as discussed above to achieve the equivalent effects.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising:
a grip section having a head section in which a treatment tool is detachably attached, and
a drive section detachably connected to the grip section,
said grip section further comprising:
a casing having a front casing portion and a rear casing portion, said front casing portion being slanted at an obtuse angle with respect to said rear casing portion and the casing being continuous,
a first rotary shaft rotatably supported in the rear casing portion,
a cylindrical jacket extending from the head section, and arranged and fixed in the front casing portion toward said first rotary shaft, said jacket being provided with an engagement groove on its circumferential surface, and
a second rotary shaft rotatably supported in said jacket, and operatively connected to the treatment tool at one end and to said first rotary shaft at the other end via a gear,
wherein driving force from said drive section is transmitted by said first and second rotary shafts to the head section to drive the treatment tool,
wherein said grip section further comprises engaging means disposed in the rear casing portion and comprising an engagement rod, said engagement rod disposed generally in parallel with the first rotary shaft, displaceable toward the front casing portion, and detachably engaging said engagement groove on the jacket,
wherein said jacket arranged in the front casing portion is fixed therein by engagement of said engagement rod in said engagement groove on the jacket.

2. The dental handpiece according to claim 1, wherein said grip section further comprises a cylindrical outer jacket fixed on the circumferential surface of the jacket,
wherein said engagement groove on the jacket comprises a circumferential groove formed in the circumferential surface of the jacket at a location facing to the interior of the rear casing portion, and a slot formed through said outer jacket at a location corresponding to and allowing access to the circumferential groove of the jacket,
wherein said engaging means further comprises engagement fixing means for fixing said engagement rod.

3. The dental handpiece according to claim 2, wherein said circumferential groove of the jacket and a tip of the engagement rod are formed so as to interfit with each other, and said slot in the outer jacket is formed such that a circumferential surface of the engagement rod is capable of contacting an upper edge of said slot.

4. The dental handpiece according to claim 2, wherein said engagement fixing means for fixing the engagement rod comprises a threaded portion formed in a circumferential surface of the engagement rod, and a nut fixed in the rear casing portion and receiving the engagement rod therethrough, with the threaded portion of the engagement rod screwed together in the nut.

5. The dental handpiece according to claim 2, wherein said engagement rod has on its rear end face a tool engaging portion in which a driving tool is engageable.

6. The dental handpiece according to claim 1, wherein said grip section further comprises an annular or cylindrical member fit on and attached around the jacket at a location facing to the interior of the rear casing portion,
wherein said engagement groove on the jacket comprises a slit formed in the circumferential surface of said annular or cylindrical member, and
wherein said engaging means further comprises engagement fixing means for fixing said engagement rod.

7. The dental handpiece according to claim 6, wherein said annular or cylindrical member has a plurality of dents in its inner surface for holding a plurality of elastic balls therein,
wherein said annular or cylindrical member is attached around the jacket via said balls, with said dents being capable of pressing said balls toward a radial center of said jacket.

8. The dental handpiece according to claim 6, wherein said grip section further comprises a sleeve provided on the inner surface of the rear casing portion, and a spring member arranged between said sleeve and the annular or cylindrical member for thrusting the annular or cylindrical member toward the head section.

9. The dental handpiece according to claim 6, wherein engagement fixing means for fixing the engagement rod comprises a threaded portion formed in a circumferential surface of the engagement rod, and a nut provided on a circumferential surface of the sleeve and receiving and guiding the engagement rod therethrough, with the threaded portion of the engagement rod screwed together in the nut.

10. The dental handpiece according to claim 1, wherein said engagement rod is displaceable with respect to the rear casing portion connected to the front casing portion.

11. The dental handpiece according to claim 1, wherein said jacket further comprises an annular or cylindrical member fit on and attached around a remaining inner part of the jacket at a location facing to the interior of the rear casing portion,
wherein said engagement groove on the jacket comprises a slit formed in the circumferential surface of said annular or cylindrical member, and
wherein said engaging means further comprises engagement fixing means for fixing said engagement rod.

12. The dental handpiece according to claim 11, wherein said annular or cylindrical member has a plurality of dents in its inner surface for holding a plurality of elastic balls therein,
wherein said annular or cylindrical member is attached around the inner part of the jacket via said balls, with said dents being capable of pressing said balls toward a radial center of said inner part of the jacket.

13. The dental handpiece according to claim 11, wherein said grip section further comprises a sleeve provided on the inner surface of the rear casing portion, and a spring member arranged between said sleeve and the annular or cylindrical member for thrusting the annular or cylindrical member toward the head section.

14. The dental handpiece according to claim 11, wherein the engagement fixing means for fixing the engagement rod comprises a threaded portion formed in a circumferential surface of the engagement rod, and a nut provided on a circumferential surface of the sleeve and receiving and guiding the engagement rod therethrough, with the threaded portion of the engagement rod screwed together in the nut.

* * * * *